(12) United States Patent
Liang

(10) Patent No.: US 12,102,783 B1
(45) Date of Patent: Oct. 1, 2024

(54) ELECTRIC FLUSHER

(71) Applicant: Yong Liang, Zhongshan (CN)

(72) Inventor: Yong Liang, Zhongshan (CN)

(*) Notice: Subject to any disclaimer, the term of this patent is extended or adjusted under 35 U.S.C. 154(b) by 0 days.

(21) Appl. No.: 18/631,176

(22) Filed: Apr. 10, 2024

(51) Int. Cl.
*A61M 3/02* (2006.01)

(52) U.S. Cl.
CPC ... *A61M 3/0279* (2013.01); *A61M 2210/1475* (2013.01)

(58) Field of Classification Search
CPC ........ A61M 3/0279; A61M 2210/1475; A61M 3/00; A61M 2210/14; E03D 9/08; B08B 3/024; B08B 3/04; E03C 1/063; E03C 1/0408; B05B 1/18; B05B 1/185; B05B 1/24; B05B 12/002; B05B 13/069; B05B 13/0636; B05B 15/68; B05B 13/0421; B05B 15/652; B05B 3/06; B05B 3/02; B05B 3/0436; B05B 3/0413; B05B 3/0431; B05B 3/0427; B05B 3/044; A61H 35/00
See application file for complete search history.

(56) References Cited

U.S. PATENT DOCUMENTS

2021/0015314 A1* 1/2021 Sylvia ................ E03D 9/08

* cited by examiner

*Primary Examiner* — Michael J Tsai
*Assistant Examiner* — Rachel T. Smith
(74) *Attorney, Agent, or Firm* — Daniel M. Cohn; Howard M. Cohn

(57) ABSTRACT

An electric flusher configured to clean a private part of a human body is provided. The electric flusher includes a base, a flushing head, and a driving assembly. The base defines a mounting space therein. The flushing head is disposed on a top portion of the base. The driving assembly is mounted in the mounting space. The driving assembly is connected to the flushing head, so that the flushing head swings or rotates in a first direction. Alternatively, the electric flusher includes the base for holding, the flushing head disposed on the top portion of the base, and an FPC germicidal lamp mounted on an outer wall of the flushing head. The electric flusher is able to comprehensively clean the private part of the human body and effectively remove dirt and bacteria.

17 Claims, 5 Drawing Sheets

ELECTRIC FLUSHER

TECHNICAL FIELD

The present disclosure relates to a technical field of cleaners, and in particular to an electric flusher.

BACKGROUND

In daily life, a private part of a human body is generally exposed to sweat, secretions, bacteria, and other microorganisms, so the private part needs to be cleaned regularly. In order to facilitate cleaning of the private part, many kinds of vaginal cleansers are created in a market. Most of the vaginal cleaners are manual, which is troublesome to operate, making a cleaning process discontinuous and not thorough, thus bring a poor cleaning effect.

SUMMARY

Embodiments of the present disclosure provide an electric flusher that is bale to comprehensively cleaning a private part of a human body and effectively remove dirt and bacteria.

In a first aspect, a first embodiment of the present disclosure provides the electric flusher configured to clean the private part of the human body. The electric flusher comprises a base, a flushing head, and a driving assembly.

The base defines a mounting space therein. The flushing head is disposed on a top portion of the base. The driving assembly is mounted in the mounting space. The driving assembly is connected to the flushing head, so that the flushing head swings or rotates in a first direction.

In one optional embodiment, the driving assembly comprises a first motor mounted in the mounting space. An output end of the first motor is fixedly connected to a first connecting piece. The first connecting piece is connected to the flushing head.

In one optional embodiment, a fixing groove is defined on a bottom end of the flushing head. At least a portion of the first connecting piece is inserted into the fixing groove to drive the flushing head to rotate.

In one optional embodiment, the driving assembly comprises a second motor mounted in the mounting space, a second connecting piece, a swinging block, and a limiting piece. The second connecting piece comprises a mounting portion and a driving portion. The mounting portion and the driving portion are connected to each other. The mounting portion is connected to an output shaft of the second motor. An extending direction of the driving portion and an extending direction of the output shaft of the second motor are not located on a same straight line.

A first end of the swinging block is connected to the driving portion. A second end of the swinging block is connected to a bottom end of the flushing head. A limiting groove is defined on a middle portion of the swinging block.

A first end of the limiting piece is connected to the base. A second end of the limiting piece is inserted into the limiting groove to connect to the limiting groove. The limiting piece is movably connected to the swinging block. The limiting piece and the limiting groove are extended in a second direction. The second direction is perpendicular to the first direction.

In one optional embodiment, the driving assembly further comprises a rolling bearing. The rolling bearing is disposed between the limiting piece and the swinging block.

In one optional embodiment, the electric flusher further comprises a flexible printed circuit (FPC) germicidal lamp disposed on an outer wall of the flushing head.

In one optional embodiment, water outlets are defined on an outer wall of the flushing head. The electric flusher further comprises a water suction pump. The water suction pump is mounted in the mounting space and is communicated with the water outlets.

In one optional embodiment, the flushing head comprises a housing, a water outlet nozzle, and a water outlet pipe. The housing defines a mounting cavity therein. The water outlet nozzle is mounted in the mounting cavity. The water outlet partially extends out of an outer wall of the housing from the mounting cavity. The water outlets are defined on the water outlet nozzle. A first end of the water outlet pipe is communicated with the water outlet nozzle. A second end of the water outlet pipe is communicated with the water suction pump.

In one optional embodiment, the electric flusher further comprises a water inlet pipe communicated with the water suction pump.

In one optional embodiment, the electric flusher further comprises a gravity ball and/or a filtering piece. The gravity ball is connected to one end of the water inlet pipe away from the water suction pump. When the filtering piece is provided, the filtering piece is connected to the water inlet pipe and is disposed in a water inlet end of the water inlet pipe.

In one optional embodiment, the electric flusher further comprises a water storage piece. The water storage piece is mounted on the base and is communicated with the water suction pump. The water inlet pipe and the water outlet pipe are communicated with the water suction pump through the water storage piece.

In one optional embodiment, the electric flusher further comprises a water storage bottle. The water storage bottle is detachably connected to the base. Driven by the water suction pump, water in the water storage bottle is sprayed out from the water outlets.

In one optional embodiment, the electric flusher further comprises a temperature sensor and an indicator light. The temperature sensor is electrically connected to the indicator light. The temperature sensor is disposed on the base and is configured to sense a temperature of the water in the water storage bottle. The indicator light is disposed on an outer wall of the base and is configured to indicate the temperature of the water in the water storage bottle.

In one optional embodiment, the electric flusher further comprises a control circuit board, control buttons, and a battery. The control circuit board and the battery are disposed in the mounting cavity. The water suction pump is controlled by the control circuit board. The battery is configured to supply power to the control circuit board and the water suction pump. The control buttons are disposed on an outer wall of the base and is electrically connected to the control circuit board.

In the electric flusher of the embodiment of the present disclosure, the base is convenient for a user to hold, so that the flushing head is able to conveniently wash the private part of the human body. By the driving assembly, the flushing head is able to swing or rotate in a flushing process. In this way, the flushing head covers a wider area, which ensures that the private part of the human body is cleaned more comprehensively, and removes the dirt and bacteria effectively. Swing or rotation of the flushing head makes the water spray uniformly and flush the private part, avoiding discomfort caused by high-pressure water flow in a single direction, and improve comfort. In addition, the swing or rotation of the flushing head also increases a contact area between water flows and the private part, improve a cleaning effect, reduces stimulation to the private part, and mildly and effectively cleans the private part.

In a second aspect, a second embodiment of the present disclosure provides the electric flusher configured to clean the private part of the human body. The electric flusher comprises a base, a flushing head, and an FPC germicidal lamp.

The base is configured for holding. The flushing head is disposed on a top portion of the base. The flushing head is configured to spray water to clean the private part. The FPC germicidal lamp is mounted on an outer wall of the flushing head.

In one optional embodiment, water outlets are defined on the outer wall of the flushing head. The electric flusher further comprises a water suction pump. The base defines a mounting space therein. The water suction pump is mounted in the mounting space and is communicated with the water outlets.

In one optional embodiment, the flushing head comprises a housing, a water outlet nozzle, and a water outlet pipe. The housing defines a mounting cavity therein. The water outlet nozzle is mounted in the mounting cavity. The water outlet partially extends out of an outer wall of the housing from the mounting cavity. The water outlets are defined on the water outlet nozzle. A first end of the water outlet pipe is communicated with the water outlet nozzle. A second end of the water outlet pipe is communicated with the water suction pump.

In one optional embodiment, the electric flusher further comprises a water inlet pipe communicated with the water suction pump.

In one optional embodiment, the electric flusher further comprises a gravity ball and/or a filtering piece. The gravity ball is connected to one end of the water inlet pipe away from the water suction pump. When the filtering piece is provided, the filtering piece is disposed on the gravity ball and is disposed in a water inlet end of the water inlet pipe.

In the electric flusher of the embodiment of the present disclosure, the base is convenient for the user to hold, so that the flushing head is convenient for cleaning.

According to the present disclosure, the FPC germicidal lamp is disposed on the outer wall of the flushing head, so that hygiene performance of the electric flusher is improved. By killing bacteria and viruses, the FPC germicidal lamp reduces a risk of cross infection, ensures a quality of the water for flushing, and provides a clean and sanitary flushing experience.

BRIEF DESCRIPTION OF DRAWINGS

In order to clearly describe technical solutions in the embodiments of the present disclosure, the following will briefly introduce the drawings that need to be used in the description of the embodiments or the prior art. Apparently, the drawings in the following description are merely some of the embodiments of the present disclosure, and those skilled in the art are able to obtain other drawings according to the drawings without contributing any inventive labor.

Figure 1:
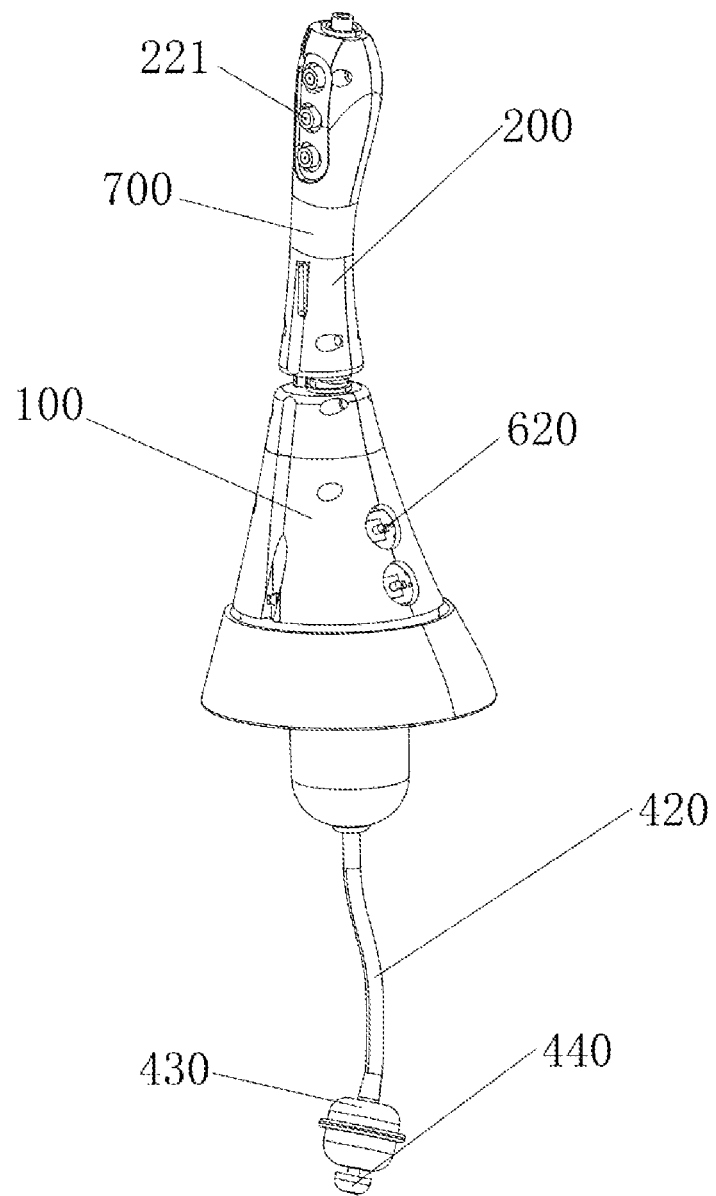
FIG. 1 is a schematic diagram of an electric flusher according to one embodiment of the present disclosure.

In the drawings: 10—electric flusher; 100—base; 200—flushing head; 210—housing; 220—water outlet nozzle; 221—water outlet; 230—water outlet pipe; 300—driving assembly; 310—first motor; 320—first connecting piece; 330—second motor; 340—second connecting piece; 341—mounting portion; 342—driving portion; 350—swinging block; 351—limiting groove; 360—limiting piece; 410—water suction pump; 420—water inlet pipe; 430—gravity ball; 440—filtering piece; 500—water storage piece; 610—control circuit board; 620—control button; 630—battery; 700—FPC germicidal lamp.

The realization of purposes, functional features, and advantages of the present disclosure is further described with reference to the embodiments and the accompanying drawings.

DETAILED DESCRIPTION

In order to make the purpose, technical solutions, and advantages of the present disclosure clear, the following section will further describe the embodiments of the present disclosure in detail with reference to the accompanying drawings.

When the following description refers to the drawings, the same numbers in different drawings refer to the same or similar elements unless otherwise indicated. The implementations described in the following exemplary embodiments do not represent all implementations consistent with the present disclosure. Rather, they are merely examples of apparatus and methods consistent with certain aspects of the present disclosure, as detailed in the appended claims.

It should be understood in the description of the present disclosure that terms such as "first" and "second" are only used for the purpose of description, rather than being understood to indicate or imply relative importance or hint the number of indicated technical features. Thus, the feature limited by "first" and "second" can explicitly or impliedly include at least one feature. Unless otherwise indicated, the term "a plurality of" means two or more. The term "and/or" depict relationship between associated objects and there are three relationships thereon. For example, A and/or B may indicate A exists alone, A and B exist at the same time, and B exists alone. The character "/" generally indicates that the associated object is alternative. The terms "first", "second", "third", etc. in the present disclosure are used only to distinguish similar objects and do not imply a specific ordering of objects.

Unless otherwise defined, all technical and scientific terms used herein have the same meaning as commonly understood by those skilled in the art of the present disclosure. The terminology used in the specification is for the purpose of describing specific embodiments only and is not intended to limit the present disclosure. As used herein, the term "and/or" includes any and all combinations of one or more of the associated listed items.

Embodiment 1

In a first aspect, as shown in FIG. 1, embodiments of the present disclosure provide an electric flusher 10 configured to clean a private part of a human body. The electric flusher 10 comprises a base 100, a flushing head 200, a water suction pump, and a driving assembly 300.

The base 100 defines a mounting space therein (not shown in the drawings).

In some embodiments, the base 100 comprises a first shell and a second shell, and the first shell and the second shell are connected to enclose the mounting space. The first shell detachably connected to the second shell. For example, the first shell is snapped with the second shell, that is, one of the first shell and the second shell comprises a snapping piece, the other one of the first shell and the second shell comprises a hook, and the first shell and the second shell are fastened together by hooking the hook on the snapping piece. Such connection form is simple to assemble the base 10. For another example, a first connecting hole is defined on the first shell, a second connecting hole corresponding to the first connecting hole is defined on the second shell, and a fastener is sequentially inserted into the second connecting hole and the first connecting hole, so as to connect the first shell and the second shell together. The fastener may be a threaded piece such as a screw or a bolt, and a connection manner between the first shell and the second shell is not specifically limited therein.

In some embodiments, the base 100 is in a conical structure or in a cylindrical structure, which facilitates the user to grasp and facilitate a cleaning operation.

The flushing head 200 is disposed on a top portion of the base 100. Water outlets 221 are defined on an outer wall of the flushing head 200. The water outlets are configured to spray water to clean the private part of the human body. In some embodiments, the flushing head 200 comprises a housing 210, a water outlet nozzle 220, and a water outlet pipe 230. The housing 210 defines a mounting cavity therein. The water outlet nozzle 220 is mounted in the mounting cavity. The water outlet partially extends out of an outer wall of the housing 210 from the mounting cavity. The water outlets 221 are defined on the water outlet nozzle 220. A first end of the water outlet pipe 230 is communicated with the water outlet nozzle 220. A second end of the water outlet pipe 230 is communicated with the water suction pump 410. In other embodiments, the water outlet nozzle 220 and the water outlet pipe 230 are integrated with the housing 210.

It should be noted that the housing 210 is made of a flexible material, such as polyethylene (PE), polypropylene (PP), polyvinyl chloride (PVC), rubber, silicone, etc., so that the housing 210 have a certain softness, which is convenient to attach to the private part of the human body for cleaning. Furthermore, the housing 210 is of a cylindrical structure, which is convenient to extend into the private part of the human body for cleaning.

The water suction pump 410 is mounted in the mounting space and is communicated with the water outlets 221. The water suction pump 410 is communicated with the water outlets on the water outlet nozzle 220 through the water outlet pipe 230.

The driving assembly 300 is mounted in the mounting space. The driving assembly 300 is connected to the flushing head 200, so that the flushing head 200 swings or rotates in a first direction.

In the electric flusher 10 of the embodiment of the present disclosure, the base 100 is convenient for a user to hold, so that the flushing head 200 is able to conveniently wash the private part of the human body. By the driving assembly 300, the flushing head 200 is able to swing or rotate in a flushing process. In this way, the flushing head 200 covers a wider area, which ensures that the private part of the human body is cleaned more comprehensively, and removes the dirt and bacteria effectively. Swing or rotation of the flushing head 200 makes the water spray uniformly and flush the private part, avoiding discomfort caused by high-pressure water flow in a single direction, and improve comfort. In addition, the swing or rotation of the flushing head 200 also increases a contact area between water flows and the private part, improve a cleaning effect, reduces stimulation to the private part, and mildly and effectively cleans the private part.

Figure 5:
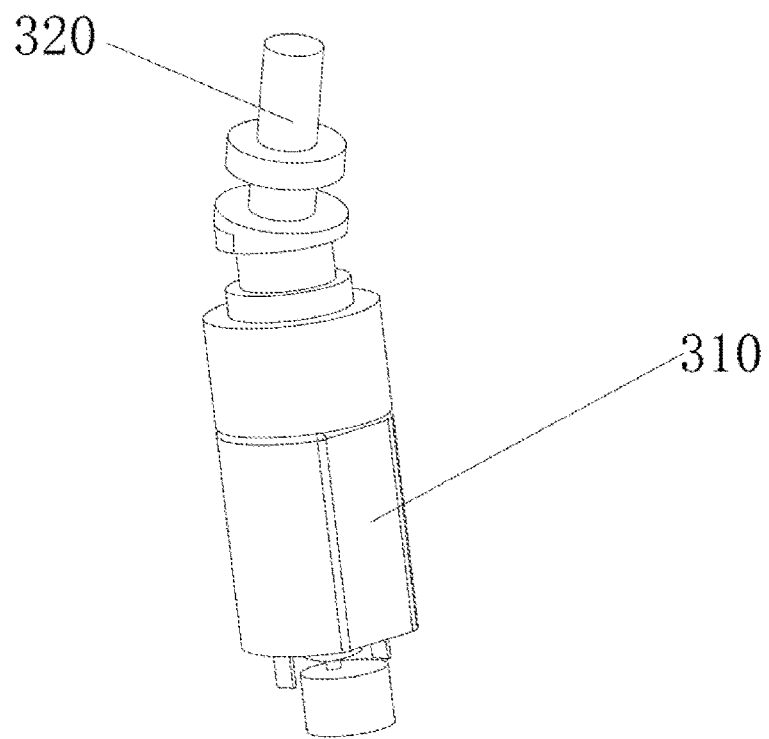
FIG. 5 is a schematic diagram of a first embodiment of a driving assembly according to one embodiment of the present disclosure.
Figure 6:
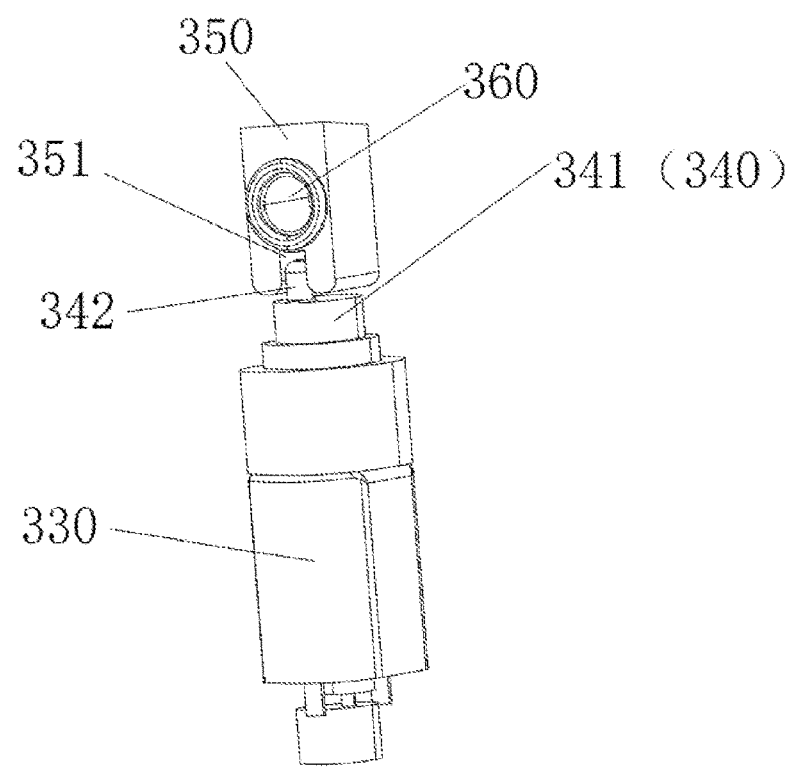
FIG. 6 is a schematic diagram of a second embodiment of the driving assembly according to one embodiment of the present disclosure.

In some embodiments, as shown in FIG. 5, the driving assembly 300 comprises a first motor 310 and a first connecting piece 320. The first motor 310 is mounted in the mounting space and is connected to the housing 210. An output end of the first motor 310 is fixedly connected to the first connecting piece 320. One end of the first connecting piece 320 away from the first motor 310 is connected to the flushing head 200. The first connecting piece 320 is a coupling, a universal joint, or other component. By such arrangement, the first motor 310 and the first connecting piece 320 drive the flushing head 200 to rotate.

Furthermore, a fixing groove (not shown in the drawings) is defined on a bottom end of the flushing head 200. At least a portion of the first connecting piece 320 is inserted into the fixing groove, which makes the flushing head 200 and the first connecting piece 320 easy to install and disassemble, and enables the user to conveniently maintain and clean the electric flusher.

In some embodiments, the driving assembly 300 comprises a second motor 330, a second connecting piece 340, a swinging block 350, and a limiting piece 360. The second motor 330 is mounted in the mounting space and is connected to the base 100. The second connecting piece 340 comprises a mounting portion 341 and a driving portion 342. The mounting portion 341 and the driving portion 342 are connected to each other. The mounting portion 341 is connected to an output shaft of the second motor 330. An extending direction of the driving portion 342 and an extending direction of the output shaft of the second motor 330 are not located on a same straight line. A first end of the swinging block 350 is connected to the driving portion 342. A second end of the swinging block 350 is connected to a bottom end of the flushing head 200. A limiting groove 351 is defined on a middle portion of the swinging block 350. A first end of the limiting piece 360 is connected to the base 100. A second end of the limiting piece 360 is inserted into the limiting groove 351 to connect to the limiting groove 351. The limiting piece 360 is movably connected to the swinging block 350. The limiting piece 360 and the limiting groove 351 are extended in a second direction. The second direction is perpendicular to the first direction.

In the electric flusher 10 of the embodiment of the present disclosure, after the mounting portion 341 and the second motor 330 are mounted, since the extending direction of the driving portion 342 and the extending direction of the output shaft of the second motor 330 are not located on the same straight line, when the second motor 330 works, the driving portion 342 is driven to rotate around a circle center of the output shaft of the second motor 330, so as to drive the swinging block to rotate. Because the limiting piece 360 is inserted into the limiting groove 351 of the swinging block, and one end of the limiting piece 360 is relatively fixed to the base 100 and extends in the second direction, the limiting piece 360 limits a movement of the swinging block in the second direction, so that the swinging block only swings in the first direction. The flushing head 200 is only allowed to swing back and forth in the first direction under driving of the swinging block, so that it is ensured that the flushing head 200 fully covers a target area of the private part in a cleaning process.

In order to improve a stability of a connection between the limiting piece 360 and the swinging block during operation, the driving assembly 300 further comprises a rolling bearing. The rolling bearing is disposed between the limiting piece 360 and the swinging block 350. It is understood that rolling bodies in the rolling bearing effectively reduce friction with an inner ring and an outer ring thereof, so that the rolling bearing reduces energy loss during high-speed operation, so that the limiting piece 360 and the swinging block are connected more stably during working, and service life of the limiting piece 360 and the swinging block is prolonged.

It should be noted that the base 100, the first connecting piece 320, the second connecting piece 340, the swinging block 350, and the limiting piece 360 are injection-molded by the PP, the PE, the PVC, etc.

Figure 2:
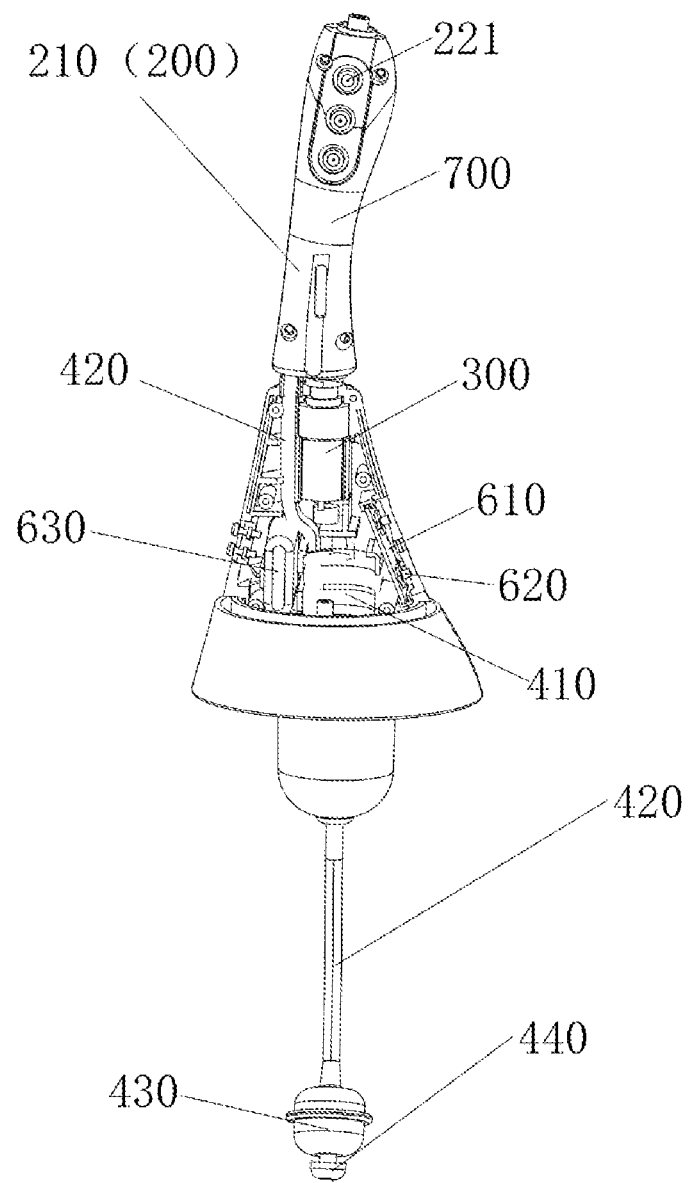
FIG. 2 is a cross-sectional schematic diagram of the electric flusher according to one embodiment of the present disclosure.
Figure 3:
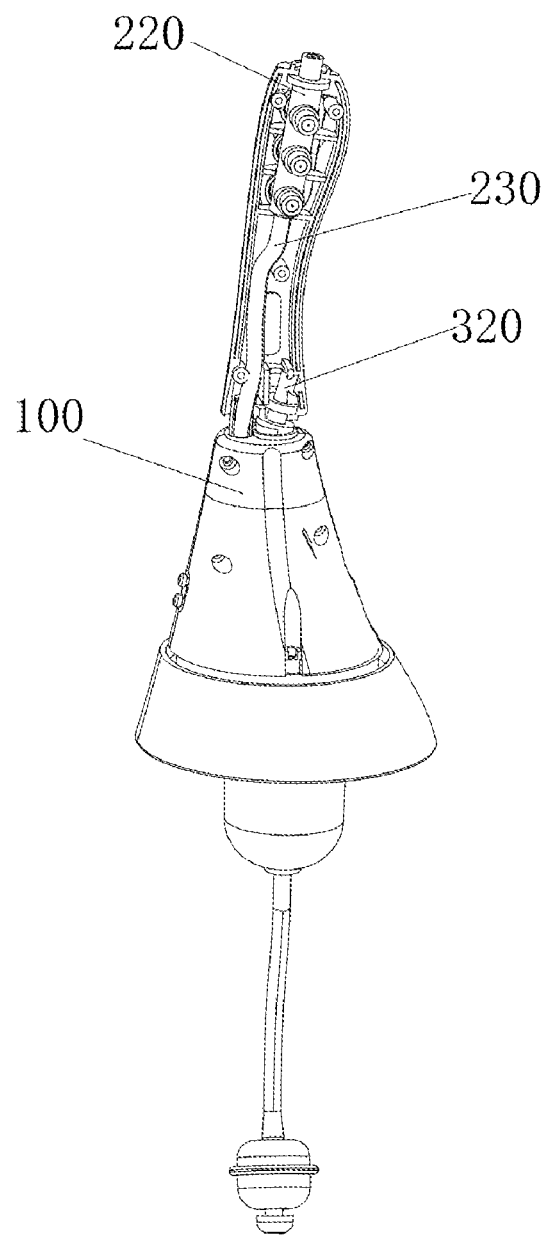
FIG. 3 is another cross-sectional schematic diagram of the electric flusher according to one embodiment of the present disclosure.

In some embodiments, as shown in FIGS. 1-3, the electric flusher 10 further comprises a water inlet pipe 420 and a gravity ball 430. The water inlet pipe 420 is communicated with the water suction pump 410. The gravity ball 430 is connected to one end of the water inlet pipe 420 away from the water suction pump 410. The water inlet pipe 420 is made of the flexible material, so that the water inlet pipe 420 is extendable into a water storage device, such as a water bottle or a water cup, so that the water suction pump 410 is able to suck the water in the water storage device. Because the water inlet pipe 420 is made of the flexible material and has a certain deformation capability, under driving of the gravity ball 430, a water suction port of the water inlet pipe 420 is allowed to contact a bottommost portion of the water bottle, which facilitates suction of the water.

Furthermore, the electric flusher 10 comprises a filtering piece 440. The filtering piece 440 is disposed on the gravity ball 430 and is disposed in a water inlet end of the water inlet pipe 420. The filtering piece 440 effectively prevents impurities from entering a water channel of the electric flusher 10, ensures a clean water source during the cleaning process, and prevents the impurities from damaging or blocking the electric flusher 10.

It should be noted that the filtering 440 may be a filter screen or a filter cotton, which is not specifically limited thereto.

Figure 4:
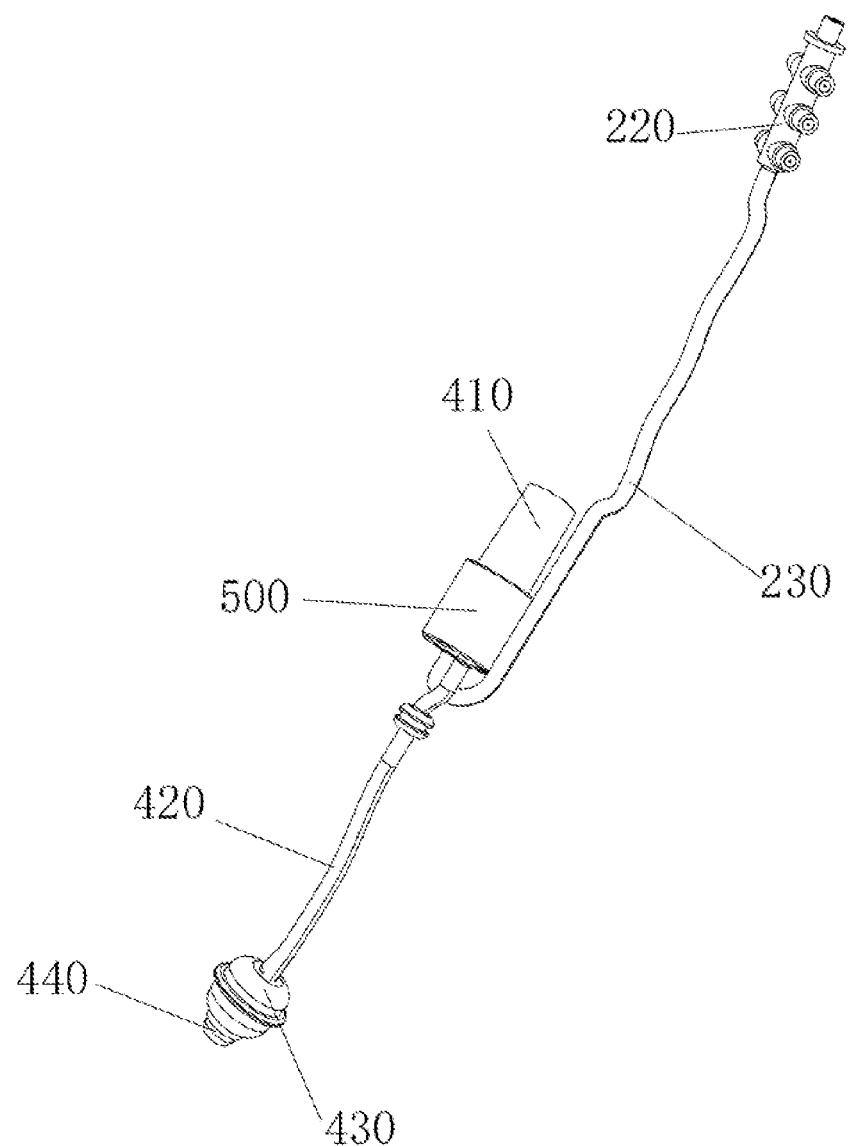
FIG. 4 is a schematic diagram of a water outlet pipe and a water suction pump according to one embodiment of the present disclosure.

As shown in FIG. 4, the electric flusher 10 further comprises a water storage piece 500. The water storage piece 500 is mounted on the base 100 and is communicated with the water suction pump 410. The water storage piece 500 defines a eater storage cavity. The water inlet pipe 420 and the water outlet pipe 230 are communicated with the water suction pump 410 through the water storage cavity. The water storage device 500 is configured to store a certain amount of water as needed for use at any time. The water storage piece 500 also balances a water pressure, so that the water sprayed from the water outlets water source can stabilize and maintain pressure equalization.

In some embodiments, the electric flusher 10 further comprises a water storage bottle (not shown). The water storage bottle is detachably connected to the base 100. The water storage bottle and the base 100 are connected by snapping structures, threads, etc., which are not specifically limited thereto. Driven by the water suction pump 410, water in the water storage bottle flows through the water inlet pipe 420, the water storage piece 500, the water outlet pipe 230, and the water outlet nozzle 220 and is sprayed out from the water outlets 221. In this way, the user is able to carry and use the electric flusher when going out or on business trips, which is convenient.

In order to avoid a temperature of the water being too high or too low to affect a user experience during the cleaning process, the electric flusher 10 further comprises a temperature sensor (not shown in the drawings) and an indicator light (not shown in the drawings). The temperature sensor is electrically connected to the indicator light. The temperature sensor is disposed on the base 100 and is configured to sense the temperature of the water in the water storage bottle. The indicator light is disposed on an outer wall of the housing 210. The indicator light is configured to indicate the temperature of the water in the water storage bottle by a color of emitted light or a flashing frequency. For example, when the temperature of the water in the water storage bottle is at a predetermined range (which may be 25-35° C.), the indicator light emits green light, and when the temperature of the water in the water storage bottle is too high or too low (which may be 0-18° C. or 38-200° C.), the indicator light emits red light. The user is reminded the temperature of the water in the water storage bottle through the color of the emitted light.

In some embodiments, as shown in FIGS. 1-3, the electric flusher 10 further comprises a control circuit board 610, control buttons 620, and a battery 630. The control circuit board 610 and the battery 630 are disposed in the mounting cavity. The temperature sensor and the water suction pump 410 is controlled by the control circuit board 610. The battery 630 is configured to supply power to the electric flusher 10. The control buttons 620 are disposed on an outer wall of the base 100. Specifically, when in use, the user transmits a signal to the control circuit board 610 by pressing the control buttons 620, and the control circuit board 610 sends a control instruction to the water suction pump 410 and switches a working state of the water suction pump 410. In some optional embodiments, the indicator light is disposed on one of the control buttons 620, so that after the user presses the control buttons 620, the electric flusher 10 enters a working mode. At this time, the temperature sensor senses the temperature of the water, the indicator light indicates whether the temperature is within the predetermined range, and the indicator light is observed on the one of the control button 620, which is convenient for the user to perform a next operation.

In one optional embodiment, the electric flusher 10 further comprises a flexible printed circuit (FPC) germicidal lamp 700 disposed on an outer wall of the flushing head 200.

The FPC germicidal lamp 700 is electrically connected to the control circuit board 610, so that the user is able to use the FPC germicidal lamp 700 through the control buttons 620. It should be noted that the FPC germicidal lamp 700 refers to a germicidal lamp 700 FAR-UVC ultraviolet having a FAR-UVC ultraviolet band having a short wavelength between 200-222 nm. Compared with a conventional ultraviolet disinfection method, FAR-UVC ultraviolet rays have a small damage to human skin and eyes, and therefore are safer and more reliable. Because a wavelength of the FAR-UVC ultraviolet rays is short, FAR-UVC ultraviolet rays can penetrate outer walls of the microorganisms to destroy their DNA and RNA structures, thereby effectively killing the microorganisms or inhibiting a growth of the microorganisms. Specifically, during use, when the water passes through the flushing head 200, the FPC germicidal lamp 700 emits the FAR-UVC ultraviolet rays, which kill the microorganisms in the air and sterilize the microorganisms in the water. In this way, hygiene performance of the electric flusher 10 is improved. By killing bacteria and viruses, the FPC germicidal lamp 700 reduces a risk of cross infection, ensure a quality of the water for cleaning and provides a clean and sanitary flushing experience.

Embodiment 2

In a second aspect, as shown in FIGS. 1-3, the present disclosure provides an electric flusher 10 configured to clean a private part of a human body. The electric flusher 10 comprises a base 100, a flushing head 200, a water suction pump 410, and an FPC germicidal lamp 700.

The base 100 defines a mounting space therein (not shown in the drawings). The base 100 comprises a first shell and a second shell, and the first shell and the second shell are connected to enclose the mounting space. In some embodiments, the base 100 is in a conical structure or in a cylindrical structure, which facilitates the user to grasp and facilitate a cleaning operation.

The flushing head 200 is disposed on a top portion of the base 100. Water outlets 221 are defined on an outer wall of the flushing head 200. The water outlets are configured to spray water to clean the private part of the human body. In some embodiments, the flushing head 200 comprises a housing 210, a water outlet nozzle 220, and a water outlet pipe 230. The housing 210 defines a mounting cavity therein. The water outlet nozzle 220 is mounted in the mounting cavity. The water outlet partially extends out of an outer wall of the housing 210 from the mounting cavity. The water outlets 221 are defined on the water outlet nozzle 220. A first end of the water outlet pipe 230 is communicated with the water outlet nozzle 220. A second end of the water outlet pipe 230 is communicated with the water suction pump 410. In other embodiments, the water outlet nozzle 220 and the water outlet pipe 230 are integrated with the housing 210.

It should be noted that the housing 210 is made of a flexible material, such as PE, PP, PVC, rubber, silicone, etc., so that the housing 210 have a certain softness, which is convenient to attach to the private part of the human body for cleaning. Furthermore, the housing 210 is of a cylindrical structure, which is convenient to extend into the private part of the human body for cleaning.

The water suction pump 410 is mounted in the mounting space and is communicated with the water outlets 221. The water suction pump 410 is communicated with the water outlets 221 on the water outlet nozzle 220 through the water outlet pipe 230.

In some embodiments, the electric flusher 10 further comprises a water inlet pipe 420 and a gravity ball 430. The water inlet pipe 420 is communicated with the water suction pump 410. The gravity ball 430 is connected to one end of the water inlet pipe 420 away from the water suction pump 410. The water inlet pipe 420 is made of the flexible material, so that the water inlet pipe 420 is extendable into a water storage device, such as a water bottle or a water cup, so that the water suction pump 410 is able to suck the water in the water storage device. Because the water inlet pipe 420 is made of the flexible material and has a certain deformation capability, under driving of the gravity ball 430, a water suction port of the water inlet pipe 420 is allowed to contact a bottommost portion of the water bottle, which facilitates suction of the water.

Furthermore, the electric flusher 10 comprises a filtering piece 440. The filtering piece 440 is disposed on the gravity ball 430 and is disposed in a water inlet end of the water inlet pipe 420. The filtering piece 440 effectively prevents impurities from entering a water channel of the electric flusher 10, ensures a clean water source during the cleaning process, and prevents the impurities from damaging or blocking the electric flusher 10.

It should be noted that the filtering 440 may be a filter screen or a filter cotton, which is not specifically limited thereto.

The FPC germicidal lamp 700 is disposed on an outer wall of the flushing head 200. The FPC germicidal lamp 700 is mounted on an outer wall of the flushing head 200. The electric flusher 10 comprises a control circuit board 610, control buttons 620, and a battery 630. The FPC germicidal lamp 700 is electrically connected to the control circuit board 610, so that the user is able to use the FPC germicidal lamp 700 through the control buttons 620. It should be noted that the FPC germicidal lamp 700 refers to a germicidal lamp 700 FAR-UVC ultraviolet having a FAR-UVC ultraviolet band having a short wavelength between 200-222 nm. Compared with a conventional ultraviolet disinfection method, FAR-UVC ultraviolet rays have a small damage to human skin and eyes, and therefore are safer and more reliable. Because a wavelength of the FAR-UVC ultraviolet rays is short, FAR-UVC ultraviolet rays can penetrate outer walls of the microorganisms to destroy their DNA and RNA structures, thereby effectively killing the microorganisms or inhibiting a growth of the microorganisms. Specifically, during use, when the water passes through the flushing head 200, the FPC germicidal lamp 700 emits the FAR-UVC ultraviolet rays, which kill the microorganisms in the air and sterilize the microorganisms in the water. In this way, hygiene performance of the electric flusher 10 is improved. By killing bacteria and viruses, the FPC germicidal lamp 700 reduces a risk of cross infection, ensure a quality of the water for cleaning and provides a clean and sanitary flushing experience.

In the electric flusher 10 of the embodiment of the present disclosure, the base 100 is convenient for the user to hold, so that the flushing head 200 is convenient for cleaning. According to the present disclosure, the FPC germicidal lamp 700 is disposed on the outer wall of the flushing head 200, so that hygiene performance of the electric flusher 10 is improved. By killing bacteria and viruses, the FPC germicidal lamp 700 reduces the risk of cross infection, ensures the quality of the water for flushing and provides the clean and sanitary flushing experience.

As shown in FIG. 4, the electric flusher 10 further comprises a water storage piece 500. The water storage piece 500 is mounted on the base 100 and is communicated with the water suction pump 410. The water storage piece 500 defines a eater storage cavity. The water inlet pipe 420 and the water outlet pipe 230 are communicated with the water suction pump 410 through the water storage cavity. The water storage device 500 is configured to store a certain amount of water as needed for use at any time. The water storage piece 500 also balances a water pressure, so that the water sprayed from the water outlets water source can stabilize and maintain pressure equalization.

In some embodiments, the electric flusher 10 further comprises a water storage bottle (not shown). The water storage bottle is detachably connected to the base 100. The water storage bottle and the base 100 are connected by snapping structures, threads, etc., which are not specifically limited thereto. Driven by the water suction pump 410, water in the water storage bottle flows through the water inlet pipe 420, the water storage piece 500, the water outlet pipe 230, and the water outlet nozzle 220 and is sprayed out from the water outlets 221. In this way, the user is able to carry and use the electric flusher when going out or on business trips, which is convenient.

In order to avoid a temperature of the water being too high or too low to affect a user experience during the cleaning process, the electric flusher 10 further comprises a temperature sensor (not shown in the drawings) and an indicator light (not shown in the drawings). The temperature sensor is electrically connected to the indicator light. The temperature sensor is disposed on the base 100 and is configured to sense the temperature of the water in the water storage bottle. The indicator light is disposed on an outer wall of the housing 210. The indicator light is configured to indicate the temperature of the water in the water storage bottle by a color of emitted light or a flashing frequency. For example, when the temperature of the water in the water storage bottle is at a predetermined range (which may be 25-35° C.), the indicator light emits green light, and when the temperature of the water in the water storage bottle is too high or too low (which may be 0-18° C. or 38-200° C.), the indicator light emits red light. The user is reminded the temperature of the water in the water storage bottle through the color of the emitted light.

In some embodiments, the control circuit board 610 and the battery 630 are disposed in the mounting cavity. The temperature sensor and the water suction pump 410 is controlled by the control circuit board 610. The battery 630 is configured to supply power to the electric flusher 10. The control buttons 620 are disposed on an outer wall of the base 100. Specifically, when in use, the user transmits a signal to the control circuit board 610 by pressing the control buttons 620, and the control circuit board 610 sends a control instruction to the water suction pump 410 and switches a working state of the water suction pump 410. In some optional embodiments, the indicator light is disposed on one of the control buttons 620, so that after the user presses the control buttons 620, the electric flusher 10 enters a working mode. At this time, the temperature sensor senses the temperature of the water, the indicator light indicates whether the temperature is within the predetermined range, and the indicator light is observed on the one of the control button 620, which is convenient for the user to perform a next operation.

In the drawings of the embodiments, the same or similar numbers correspond to the same or similar components; in the description of the present disclosure, it should be understood that terms such as "upper", "lower", "left", "right", etc. indicate direction or position relationships shown based on the drawings, and are only intended to facilitate the description of the present disclosure and the simplification of the description rather than to indicate or imply that the indicated device or element must have a specific direction or constructed and operated in a specific direction. Therefore, the terms used to describe positional relationships in the drawings are only for illustrative purposes and cannot be construed as limitations of the present disclosure. For those of ordinary skill in the art, the specific meanings of the above terms can be understood according to specific circumstances.

The above are only optional embodiments of the present disclosure and are not intended to limit the present disclosure. Any modifications, equivalent substitutions, and improvements made within the spirit and principles of the present disclosure shall be included in the protection scope of the present disclosure.

What is claimed is:

1. An electric flusher, configured to clean a private part of a human body, comprising:
   a base;
   a flushing head; and
   a driving assembly,
   wherein the base defines a mounting space therein, the flushing head is disposed on a top portion of the base, the driving assembly is mounted in the mounting space, and the driving assembly is connected to the flushing head, so that the flushing head swings or rotates in a first direction;
   wherein the driving assembly comprises a first motor mounted in the mounting space, an output end of the first motor is fixedly connected to a first connecting piece, and the first connecting piece is connected to the flushing head;
   wherein a fixing groove is defined on a bottom end of the flushing head, and at least a portion of the first connecting piece is inserted into the fixing groove to drive the flushing head to rotate.

2. The electric flusher according to claim 1, wherein the driving assembly comprises a second motor mounted in the mounting space, a second connecting piece, a swinging block, and a limiting piece, the second connecting piece comprises a mounting portion and a driving portion, the mounting portion and the driving portion are connected to each other; the mounting portion is connected to an output shaft of the second motor, and an extending direction of the driving portion and an extending direction of the output shaft of the second motor are not located on a same straight line;
   wherein a first end of the swinging block is connected to the driving portion, a second end of the swinging block is connected to a bottom end of the flushing head, and a limiting groove is defined on a middle portion of the swinging block; and
   a first end of the limiting piece is connected to the base, a second end of the limiting piece is inserted into the limiting groove to connect to the limiting groove, the limiting piece is movably connected to the swinging block, the limiting piece and the limiting groove are extended in a second direction, and the second direction is perpendicular to the first direction.

3. The electric flusher according to claim 2, wherein the driving assembly further comprises a rolling bearing, wherein the rolling bearing is disposed between the limiting piece and the swinging block.

4. The electric flusher according to claim 1, wherein the electric flusher further comprises a flexible printed circuit (FPC) germicidal lamp disposed on an outer wall of the flushing head.

5. The electric flusher according to claim 1, wherein water outlets are defined on an outer wall of the flushing head, wherein the electric flusher further comprises a water suction pump, and the water suction pump is mounted in the mounting space and is in communication with the water outlets.

6. The electric flusher according to claim 5, wherein the flushing head comprises a housing, a water outlet nozzle, and a water outlet pipe, the housing defines a mounting cavity therein, the water outlet nozzle is mounted in the mounting cavity, the water outlet partially extends out of an outer wall of the housing from the mounting cavity, the water outlets are defined on the water outlet nozzle, a first end of the water outlet pipe is in communication with the water outlet nozzle, and a second end of the water outlet pipe is in communication with the water suction pump.

7. The electric flusher according to claim 5, wherein the electric flusher further comprises a water inlet pipe in communication with the water suction pump.

8. The electric flusher according to claim 7, wherein the electric flusher further comprises a gravity ball and/or a filtering piece, the gravity ball is connected to one end of the water inlet pipe away from the water suction pump, and when the filtering piece is provided, the filtering piece is connected to the water inlet pipe and is disposed in a water inlet end of the water inlet pipe.

9. The electric flusher according to claim 5, wherein the electric flusher further comprises a water storage piece, the water storage piece is mounted on the base and is in communication with the water suction pump, and the water inlet pipe and the water outlet pipe are in communication with the water suction pump through the water storage piece.

10. The electric flusher according to claim 5, wherein the electric flusher further comprises a water storage bottle, the water storage bottle is detachably connected to the base, and when driven by the water suction pump, water in the water storage bottle is sprayed out from the water outlets.

11. The electric flusher according to claim 10, wherein the electric flusher further comprises a temperature sensor and an indicator light, the temperature sensor is electrically connected to the indicator light, the temperature sensor is disposed on the base and is configured to sense a temperature of the water in the water storage bottle, and the indicator light is disposed on an outer wall of the base and is configured to indicate the temperature of the water in the water storage bottle.

12. The electric flusher according to claim 5, wherein the electric flusher further comprises a control circuit board, control buttons, and a battery, the control circuit board and the battery are disposed in the mounting cavity, the water suction pump is controlled by the control circuit board, the battery is configured to supply power to the control circuit board and the water suction pump, and the control buttons are disposed on an outer wall of the base and is electrically connected to the control circuit board.

13. An electric flusher, configured to clean a private part of a human body, comprising:
a base;
a flushing head; and
an FPC germicidal lamp;
wherein the base is configured for holding, the flushing head is disposed on a top portion of the base, the flushing head is configured to spray water to clean the private part, and the FPC germicidal lamp is mounted on an outer wall of the flushing head;
wherein water outlets are defined on the outer wall of the flushing head, the electric flusher further comprises a water suction pump, the base defines a mounting space therein, and the water suction pump is mounted in the mounting space and is in communication with the water outlets.

14. The electric flusher according to claim 13, wherein the flushing head comprises a housing, a water outlet nozzle, and a water outlet pipe, the housing defines a mounting cavity therein, the water outlet nozzle is mounted in the mounting cavity, the water outlet partially extends out of an outer wall of the housing from the mounting cavity, the water outlets are defined on the water outlet nozzle, a first end of the water outlet pipe is in communication with the water outlet nozzle, and a second end of the water outlet pipe is in communication with the water suction pump.

15. The electric flusher according to claim 13, wherein the electric flusher further comprises a water inlet pipe in communication with the water suction pump.

16. The electric flusher according to claim 15, wherein the electric flusher further comprises a gravity ball and/or a filtering piece; the gravity ball is connected to one end of the water inlet pipe away from the water suction pump; and when the filtering piece is provided; the filtering piece is disposed on the gravity ball and is disposed in a water inlet end of the water inlet pipe.

17. An electric flusher, configured to clean a private part of a human body, comprising:
a base;
a flushing head; and
a driving assembly;
wherein the base defines a mounting space therein, the flushing head is disposed on a top portion of the base, the driving assembly is mounted in the mounting space, and the driving assembly is connected to the flushing head, so that the flushing head swings or rotates in a first direction;
wherein the driving assembly comprises a rolling bearing, a swinging block, and a limiting piece, and the rolling bearing is disposed between the limiting piece and the swinging block.

* * * * *